United States Patent [19]
Sandman et al.

[11] 4,080,332
[45] Mar. 21, 1978

[54] ELECTRICALLY CONDUCTIVE COMPOUNDS

[75] Inventors: Daniel J. Sandman, Webster; Arthur J. Epstein, Pittsford, both of N.Y.

[73] Assignee: Xerox Corporation, Stamford, Conn.

[21] Appl. No.: 700,426

[22] Filed: Jun. 28, 1976

[51] Int. Cl.$^2$ ........................................... C07D 409/04
[52] U.S. Cl. ............................................. 260/327 TH
[58] Field of Search ................................. 260/327 TH

[56] References Cited
PUBLICATIONS

Syper, et al., Bull. Acad. Pol. Sci., Chim. 23:563, (1975).

Primary Examiner—Cecilia M. S. Jaisle
Attorney, Agent, or Firm—James J. Ralabate; James P. O'Sullivan; Gaetano D. Maccarone

[57] ABSTRACT

There are described novel charge transfer compounds having high electrical conductivity which are represented by the formula $[A]_x^+ [B]_y^-$ where A is represented by the formula

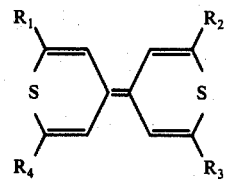

where $R_1$–$R_4$ may be the same or different and may be H or $CH_3$ and B is 7,7,8,8-tetracyanoquinodimethane, X is 1 and Y is 1 or 2.

4 Claims, No Drawings

ELECTRICALLY CONDUCTIVE COMPOUNDS

BACKGROUND OF THE INVENTION

This application relates generally to novel compositions of matter and more particularly to charge transfer compounds having high electrical conductivity.

Semiconducting materials have been found to be useful in semiconductor devices such as transistors, thermistors, rectifiers, diodes, photocells, etc. However, there are only a limited number of known organic semiconductive materials and even fewer such materials which may be characterized as having simple molecular structures which exhibit resistivities of a low order such as, for example, less than 100 ohm-cm. Conducting molecular materials are also useful in devices which include highly conductive metals such as, for example, conductive wires, layers and the like. Accordingly, there is a continuing interest in the art in new organic materials of these types.

It is therefore an object of this invention to provide novel charge transfer compounds.

It is another object of the invention to provide charge transfer compounds having high electrical conductivity.

BRIEF SUMMARY OF THE INVENTION

The foregoing objects and advantages and others are accomplished in accordance with the present invention by providing novel charge transfer compounds having high electrical conductivity which are represented by the formula $$[A]_x^+ [B]_y^-$$

where A is represented by the formula

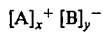

(I)

where $R_1-R_4$ may be the same or different and may be H or $CH_3$ and B is 7,7,8,8-tetracyanoquinodimethane (hereafter referred to as "TCNQ"), X is 1 and Y is 1 or 2.

The compounds of the invention are typically dark colored and demonstrate high conductivity, i.e. they are characterized by low resistivity. Accordingly, these compounds are potentially useful in any application where semiconducting materials are utilized such as transistors, rectifiers, diodes, etc. or where conducting materials are employed such as, for example, as a support substrate in electrophotographic imaging members.

The organosulfur electron donor compounds utilized according to the invention may be synthesized by methods known in the art. $\delta,\delta'$-bithiopyrylene (I,$R_1$-$R_4$=H), referred to hereafter as "BTP", can be synthesized by the method reported by Hünig et al, *J. Liebigs Ann. Chem.*, 1036 (1973) as shown in (1):

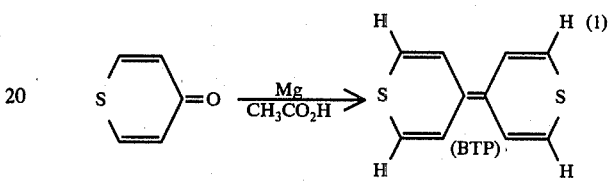

2,2',6,6'-tetramethyl-4,4'-bithiopyrylene (I,$R_1$-$R_4$ = $CH_3$), hereafter referred to as "TMBTP" can be synthesized according to the methods shown in (2)

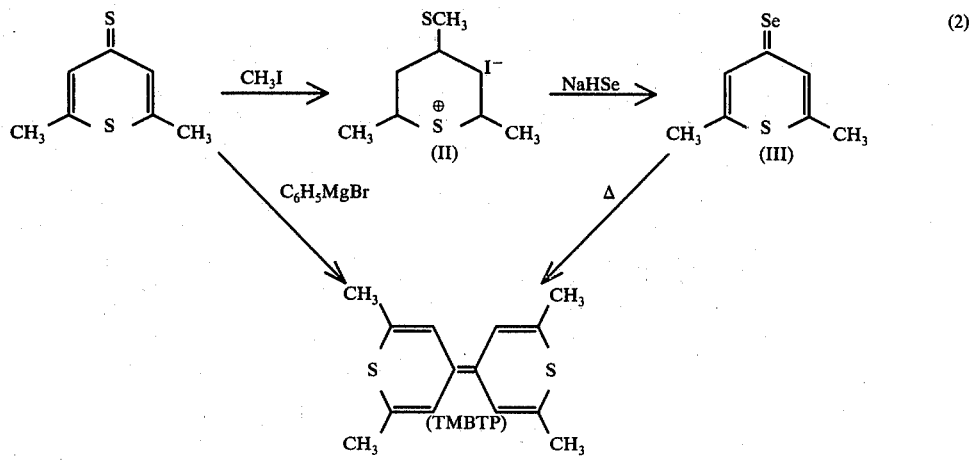

The synthesis of TMBTP via the formation of 2,6 dimethyl-4-seleno-1,4-thiapyrone (III) is reported by G. Traverso, *Ann. Chem. Rome*, 47, 1244, (1957).

DESCRIPTION OF THE PREFERRED EMBODIMENTS

The invention will now be described with respect to specific preferred embodiments thereof it being understood that these are illustrative and the invention is not limited thereto.

PREPARATION OF BTP (I, $R_1$-$R_4$ = H)

To 54ml of an acetic acid solution of 1-thio-4-pyrone (8.0gms; 0.0714 mole) containing 1 drop of conc. hydrochloric acid which was being stirred mechanically at a temperature of about 15° C under $CO_2$ atmosphere there was added in portions 8.0gms magnesium dust (0.329gm-atom) and 100ml frozen acetic acid. The temperature of the reaction was maintained near 15° C until the end when it approached 25° C. The reaction mixture was poured into 300ml. of a 10% sodium bisulfite solution saturated with $CO_2$. The yellow solid reaction product was isolated by suction filtration, washed with 150ml of 1% sodium hydroxide solution and 100ml water. The solid was dried for 5 hours over potassium hydroxide and phosphorous pentoxide and then extracted with four 50ml portions of hot cyclohexane. The yellow solid was further soxhlet extracted overnight with cyclohexane. The cyclohexane extracts were combined and evaporated under reduced pressure. The solid product was collected by suction filtration. About 100–200mg of product with a M.P. of 180°–185° C (dec.) were obtained. The product was further purified by gradient sublimation (95°–100° C at $10^{-6}$mm) to give a red-orange solid, M.P. 193°–197° C (dec.).

The product had an infrared spectrum (recorded in Nujol) in agreement with that reported by Hunig et al and its ultraviolet-visible spectrum, obtained in acetonitrile solution containing one drop of triethylamine, exhibited the following: $\lambda$max(log $\epsilon$): 386(4.772), 367(4.600), 346 sh (4.252). The mass spectrum showed parent and base peak at m/e 192. The elemental analysis was: 62.77% C; 4.34% H; 33.15% S. $C_{10}H_8S_2$ requires 62.46% C; 4.19% H; and 33.35% S.

PREPARATION OF (BTP)-(TCNQ)

A solution of 25.4mg BTP in 4ml acetonitrile and 2ml benzene was mixed with a solution of 26mg TCNQ in 5ml acetonitrile at room temperature. The mixture turned green and was stored in a refrigerator for ½ hour. A dark purple solid, 43mg, M.P. 195°–200° C (dec.) was isolated by suction filtration. The elemental analysis was: 66.59% C; 3.11% H; and 13.98% N. $C_{22}H_{12}S_2N_4$ requires 66.64% C; 3.05% H; and 14.13% N.

A compressed pellet of the solid was made and four conductive paint contacts were applied. Two contacts were connected to a current source and the other two to a volt meter through wires and the resistivity was measured when a current was passed through it. The pellet had a conductivity of 1.2 (ohm-cm)$^{-1}$.

PREPARATION OF (BTP)-(TCNQ)$_2$

A solution of 16.3mg BTP (0.0848 mole) in a mixture of 10ml of acetonitrile and 12ml benzene was added to solution of 35.3mg TCNQ (0.173 mole) in 12ml of acetonitrile when both solutions were at room temperature. After storing the reaction mixture in a refrigerator for about ½ hour the dark solid reaction product was collected by suction filtration and vacuum dried to give 46.6mg of product, M.P. 215°–220° C (dec.). Elemental analysis was: 68.24% C; 2.79% H, 18.38% N and 10.54% S. $C_{34}H_{16}N_8S_2$ requires: 67.98% C; 2.68% H; 18.65% N and 10.68% S.

A compressed pellet of this solid had a conductivity of 8.1 (ohm-cm)$^{-1}$ as measured by the previously described technique.

PREPARATION OF 2,6 DIMETHYL-4-THIOMETHYL-1-THIAPYRYLIUM IODIDE (II)

A solution of 1.2 grams (7.7 mmole) of 2,6-dimethyl-4-thio-1,4-thiapyrone [prepared according to the method described by Arndt et al, *Rev. Fac. Sci. Univ. Istanbul, A*13, 57 (1948); *Chem. Abstr.*, 42, 4176 (1948)] in 110ml acetone was heated with 2.28 grams (16 mmole) methyl iodide. The mixture solidified and an additional 5ml acetone was added. After cooling to room temperature the mixture was filtered and air dried to give 1.8 grams of a greenish yellow-brown solid M.P. 157°–159° C (dec.). Elemental analysis of the product was: 32.29% C and 3.65% H. $C_8H_{11}IS_2$ requires 32.22% C and 3.72% H.

PREPARATION OF TMBTP (I, R$_1$-R$_4$ = CH$_3$)

A mixture of 12.3 grams (0.0463 mole) of 2,6-dimethyl-4-thiomethyl-1-thiapyrylium iodide (III) in 246 ml water was filtered into a solution of 6 grams (0.15 mole) sodium hydroxide in 28ml water saturated with hydrogen selenide with mechanical stirring at 0° C under nitrogen in the dark. After 2 hours the mixture was filtered and washed with ice water. The solid residue was taken up in five 100ml portions of ether and the ether solution was washed twice with water, dried over magnesium sulfate, filtered and evaporated at reduced pressure. The residue was extracted with a total of 1500ml of reagent grade hexane kept below 50° C and the solutions were placed in a refrigerator to crystallize out (III). The reaction product (III), M.P. 110°–112.5° C, was obtained in a 15–20% yield.

The mother liquors of (III) when evaporated at reduced pressure precipitate both (III) and TMBTP and such mixtures can be converted to TMBTP in the same manner as (III) alone as follows: a solution of 1.10 grams (III) in 105ml cyclohexane was heated at reflux under nitrogen for 4 hours, filtered while hot and then cooled in a refrigerator. The product isolated by suction filtration had a M.P. 210°–217° C (dec.). A second batch prepared in the same manner had a M.P. 212°–219° C (dec.). The yield of TMBTP was 20% based on 2,6-dimethyl-1-thio-1,4-thiapyrone. The TMBTP was further purified by recrystallization from cyclohexane followed by gradient sublimation twice on Kapton at 110°–120° C at 10$^{-6}$ mm. The purified TMBTP has a M.P. 218°–222.5° C. The same melting point was observed on cooling of the melt and reheating. The elemental analysis was: 67.89% C; 6.69% H; and 25.58% S. $C_{14}H_{16}S_2$ requires: 67.69% C; 6.49% H; and 25.82% S. The mass spectrum of the product showed parent and base peak at m/e 248 (calculated value 248). The ultraviolet-visible spectrum obtained in acetonitrile solution containing one drop of triethylamine, exhibited the following: $\lambda$max (log$\epsilon$): 397 (4.84), 376 (4.68), 357 sh (4.36).

The TMBTP prepared according to the method described above was used in the preparation of the (TMBTP)-(TCNQ) compounds described below herein.

TMBTP has also been prepared via 2,6-dimethyl-4-thio-1,4-thiapyrone and phenylmagnesium bromide as follows: to a solution of 15.6gms (0.01 mole) 2,6-dimethyl-1-thio-1,4-thiapyrone in 15ml anhydrous ether under nitrogen was added 6ml of a 3M solution of phenylmagnesium bromide in ether. The mixture was refluxed for two hours at which time thin layer analysis showed the absence of reactant. The ether solution was poured off and mixed with 50ml benzene. This mixture was hydrolyzed with 100ml water and the organic layer was dried with magnesium sulfate, filtered, and evaporated to give a brown solid, 74mg, which was purified in the manner described above and had an absorption spectrum in agreement with that of the TMBTP prepared above. The elemental analysis was: 67.18% C and 6.47% H. $C_{14}H_{16}S_2$ requires: 67.69% C and 6.49% H.

PREPARATION OF (TMBTP)-(TCNQ)

1. A solution of 24.2mg (11.85 mmole) TCNQ in 11ml acetonitrile was mixed with a solution of 35.0mg (14.2 mmole) TMBTP in 16ml acetonitrile with the solutions at room temperature. A green color appeared immediately and the mixture was cooled in a refrigerator. A black solid was collected by suction filtration and vacuum dried to give 29mg of product, M.P. 170°–172° C (dec.). The elemental analysis was: 69.74% C; 4.43% H; 12.78% N and 13.23% S. $C_{20}H_{20}N_4S_2$ requires: 69.00% C; 4.45% H; 12.38% N and 14.17% S. Single crystals of this sample had conductivity ranging from $3.4 \times 10^{-4}$ to $1.2 \times 10^{-3}$ (ohm-cm)$^{-1}$ at room temperature and a compressed pellet had a conductivity of $1.75 \times 10^{-5}$ (ohm-cm)$^{-1}$ when measured as described above.

2. A solution of 37.8mg (0.15 mmole) TMBTP in 1ml dimethylformamide (which had been freshly vacuum distilled) and a solution of 30.2mg (15 mmole) TCNQ in 5ml dimethylformamide were mixed at room temperature and cooled in a refrigerator. The product was filtered, washed with acetonitrile and hexane and vacuum dried to give 16mg of product, M.P. 170°–172° C (dec.). Elemental analysis was: 68.99% C; 4.72% H and 13.51% S.

It should be noted that when the reaction was carried out in hot dimethylformamide no product was obtained. Hence, the materials used to form the compounds of the invention should be mixed together at room temperature since if they are heated to elevated temperatures decomposition may occur, particularly in those compounds prepared with TMBTP.

PREPARATION OF (TMBTP)–(TCNQ)$_2$

A solution of 24.9mg (0.1 mmole) TMBTP in 10ml acetonitrile was mixed with a solution of 44.8mg (0.219 mmole) TCNQ in 20ml acetonitrile at room temperature. A green solution formed and it was placed in a refrigerator to cool. A black powder, 50mg was isolated by suction filtration, washed with ether and vacuum dried. Elemental analysis was: 69.36% C; 3.78% H; 16.98% N and 10.12% S. $C_{38}H_{24}S_2N_8$ requires: 69.49% C; 3.69% H; 17.06% N and 9.76% S. A compressed pellet of the product had a conductivity of 0.5 (ohm-cm)$^{-1}$ when measured by the technique described above.

The preparation of (TMBTP)$_2$(TCNQ)$_3$ was attempted as follows: a solution of 26.3mg (0.106 mmole) of TMBTP in 12ml acetonitrile was mixed in a solution of 30.5mg. (0.15 mmole) TCNQ in 12ml acetonitrile at room temperature. The mixture was cooled in a refrigerator, and 47mg of a dark solid. M.P. 158°–162° C (dec.) was isolated by suction filtration. Elemental analysis was: 69.30% C, 4.17% H; 15.13% N and 11.66% S. $C_{64}H_{44}N_{12}S_4$ requires: 69.29% C; 4.00% H; 15.15% N and 11.56% S. A compressed pellet of the product had a conductivity of 0.18 (ohm-cm)$^{-1}$ when measured by the abovedescribed technique. While the product gave a satisfactory elemental analysis for (TMBTP)$_2$(TCNQ)$_3$, x-ray powder diffraction analysis indicated that the product was a mixture of the (TMBTP) (TCNQ) and (TMBTP) (TCNQ)$_2$ compounds described above.

What is claimed is:

1. A compound represented by the formula

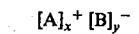
$[A]_x^+ [B]_y^-$ where A is represented by the formula

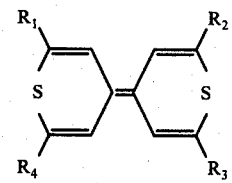

where $R_1$–$R_4$ may be the same or different and may be H or CH$_3$ and B is 7,7,8,8-tetracyanoquinodimethane, X is 1 and Y is 1 or [2$_x$] 2, wherein when $R_1$–$R_4$ are CH$_3$, Y is 2.

2. A compound represented by the formula $[A]_x^+ [B]_y^-$ where A is represented by the formula

and B is 7,7,8,8-tetracyanoquinodimethane, X is 1 and Y is 1.

3. A compound represented by the formula $[A]_x^+ [B]_y^-$ where A is represented by the formula

and B is 7,7,8,8-tetracyanoquinodimethane, X is 1 and Y is 2.

4. A compound represented by the formula $[A]_x^+ [B]_y^-$ where A is represented by the formula

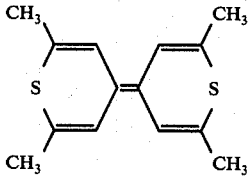

and B is 7,7,8,8-tetracyanoquinodimethane, X is 1 and Y is 2.

* * * * *